(12) United States Patent
Codignola et al.

(10) Patent No.: US 6,565,754 B1
(45) Date of Patent: May 20, 2003

(54) PROCESS FOR THE PRODUCTION AND PURIFICATION OF AROMATIC ACIDS

(76) Inventors: Franco Codignola, Corso Lodi 59, 20139 Milan (IT); Antonio Moro, Residenza Parco 161, 20090 Segrate, Milan (IT)

( * ) Notice: Subject to any disclaimer, the term of this patent is extended or adjusted under 35 U.S.C. 154(b) by 0 days.

(21) Appl. No.: 09/958,692
(22) PCT Filed: Apr. 13, 2000
(86) PCT No.: PCT/EP00/03338
  § 371 (c)(1),
  (2), (4) Date: Nov. 15, 2001
(87) PCT Pub. No.: WO00/63146
  PCT Pub. Date: Oct. 26, 2000

(30) Foreign Application Priority Data

Apr. 16, 1999 (IT) .......................... MI99A0798

(51) Int. Cl.$^7$ ................................ C02F 1/42
(52) U.S. Cl. ................ 210/684; 210/688; 210/912
(58) Field of Search ............... 210/661, 684, 210/688, 912

(56) References Cited

U.S. PATENT DOCUMENTS

| | | | |
|---|---|---|---|
| 3,168,485 A | | 2/1965 | Knobloch et al. |
| 5,112,992 A | | 5/1992 | Belmonte et al. |
| 6,160,170 A | * | 12/2000 | Codignola .................. 562/413 |

FOREIGN PATENT DOCUMENTS

WO          85/02353          6/1985

* cited by examiner

*Primary Examiner*—Chester T. Barry
(74) *Attorney, Agent, or Firm*—Nixon & Vanderhye

(57) ABSTRACT

A description is given here of a novel process for the production of monocarboxylic and polycarboxylic aromatic acids by the catalytic oxidation in homogeneous phase of aromatic compounds carrying at least one oxidizable substituent group attached directly to the carbon atom of the corresponding aromatic nucleus. The process comprises a purification step in which the crude product resulting from the oxidation stage is supplied to a filling column containing a bed of material having a high adsorbent power with respect to hafnium and/or zirconium polyoxides, operating at a temperature of from 200 to 300° C. and at a pressure of from 30 to 90 barg.

12 Claims, 1 Drawing Sheet

PROCESS FOR THE PRODUCTION AND PURIFICATION OF AROMATIC ACIDS

Figure 1:
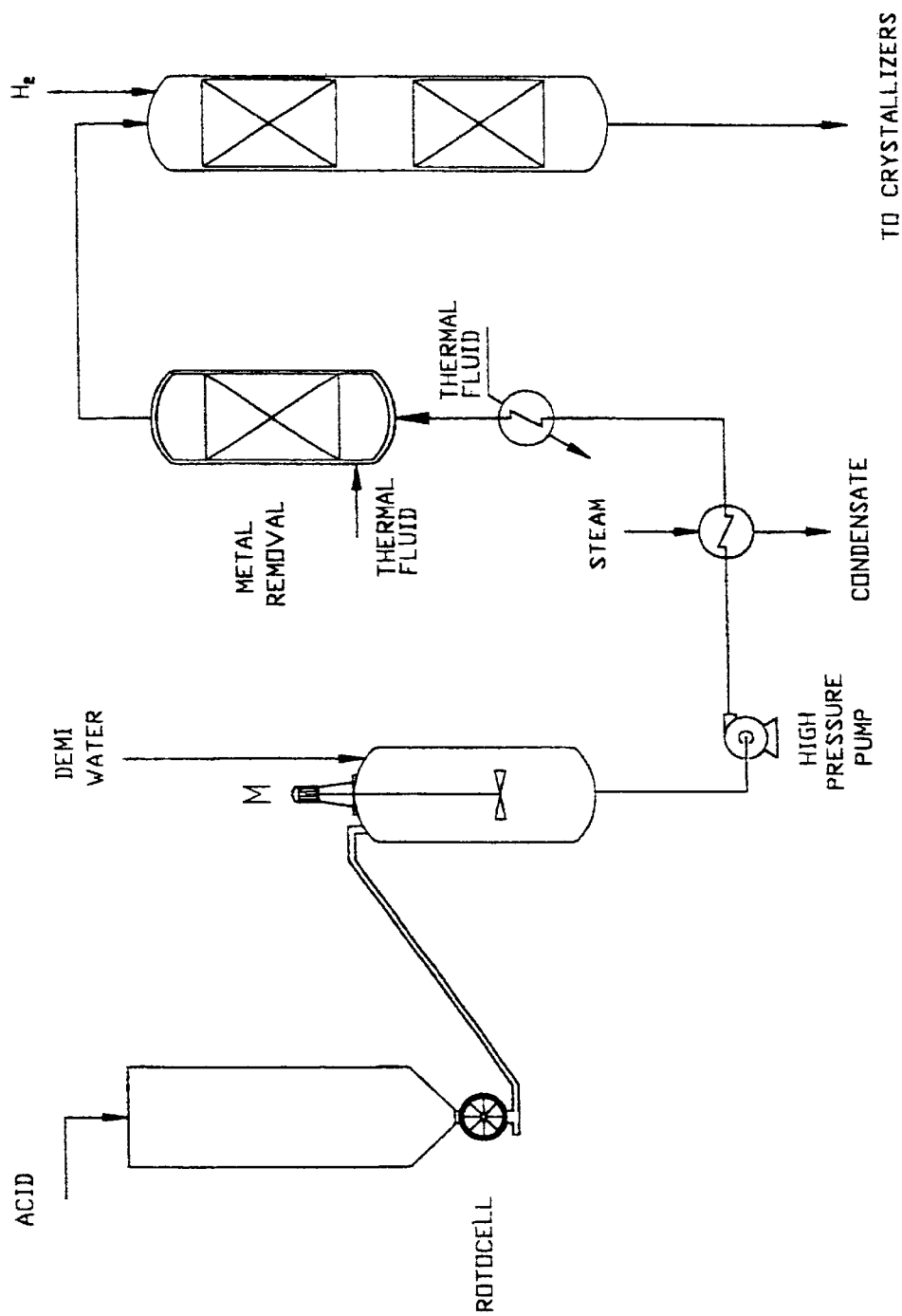

The present invention relates to a novel process for the production and subsequent purification of monocarboxylic and polycarboxylic aromatic acids by the catalytic oxidisable substituent group attached directly to the carbon atom of the corresponding aromatic nucleus.

FIELD OF THE INVENTION

Processes for the production of monocarboxylic and polycarboxylic aromatic acids are well known in the literature. They are normally carried out in liquid phase, operating either continuously or discontinuously and using as substrates aromatic compounds carrying at least one oxidisable substituent group attached directly to the carbon atom of the corresponding aromatic nucleus, where the expression "oxidisable substituent group" is intended to indicate any substituent in which a carbon atom is bonded directly to the aromatic nucleus and which, as a result of oxidation, is converted into a carboxyl group.

The oxidising agent is generally gaseous molecular oxygen, preferably diluted with an inert gas; for obvious reasons of practicality, air (optionally enriched with molecular oxygen) is the gaseous mixture most commonly used for this purpose. The oxidation reaction is normally carried out using as solvent an aqueous organic acid, preferably acetic acid, normally with a water content of from 2 to 15%.

Those reactions are carried out in the presence of a catalytic complex generally composed of one or more metals, normally in the form of salts soluble in the reaction solvent, and a suitable activator. The metal performs the function of catalysing the actual oxidation reaction while the activator is used to return the metal (which undergoes a reduction in its oxidation number during catalysis) to its original valency, thus enabling it to regain and exert its catalytic activity. The activator may itself be a metal, in which case it also will preferably be present in the form of a salt soluble in the reaction medium; alternatively, it is possible to use organic compounds having carbonyl functions, such as ketones or aliphatic aldehydes, preferably acetaldehyde, or molecular bromine.

British patent GB-1063964 describes a process for the production of monocarboxylic and polycarboxylic aromatic acids at temperatures of preferably from 80 to 130° C. and pressures of from 1 to 60 kg/cm² by means of a catalytic complex substantially based on zirconium and cobalt.

U.S. Pat. No. 5,112,992 describes the production of aromatic acids at temperatures of from 100 to 275° C., using metals from groups IIIA and IVA of the periodic table of elements (groups IIIB and IVB according to the new notation adopted, for example, by Perry, *Chemical Engineers' Handbook*, VI edition, 1984), in particular zirconium and hafnium, in order to increase the kinetics of oxidation reactions that use catalytic complexes based on cobalt and manganese in the presence of bromine as the activator.

International patent application WO 98/29378 describes a catalytic complex comprising:
1. at least one metal having a valency higher than 2 which belongs to group VIIIA of the periodic table of elements, preferably ruthenium, iridium, palladium, platinum; and/or at least one metal from group VIIA, preferably rhenium; and/or cerium; and
2. at least one metal from group IVA of the periodic table of elements, preferably zirconium and/or hafnium;

where the catalytic pair cerium-zirconium constitutes the preferred complex for implementing the invention.

N.B. groups VIIIA, VIIA and IVA indicated above correspond, respectively, to groups VIII, VIIB and IVB according to the new notation adopted, for example, by Perry, *Chemical Engineers' Handbook*, VI edition.

The catalytic complex described in WO 98/29378 is used for the production of monocarboxylic and polycarboxylic aromatic acids, preferably from meta- and para-xylene, operating at temperatures of from 90 to 150° C., preferably from 105 to 115° C., and at pressures of from 1 to 20 barg, preferably from 2 to 5 barg.

Monocarboxylic and polycarboxylic aromatic acids have a very low solubility in the solvents conventionally used in oxidation reactions of the type described above; therefore, they can be readily isolated from the reaction medium by simple filtration.

Once separated by filtration, the crude acid so obtained normally has to be purified of any secondary products of the oxidation reaction, generally aromatic aldehydes, formed by partial oxidation of the aromatic starting derivatives and, as such, difficult to separate from the desired end products; the crude terephthalic acid, for example, generally obtained by oxidation of para-methylacetophenone or para-xylene, normally contains a not inconsiderable amount of para-carboxybenzaldehyde which, because it is relatively similar to terephthalic acid from a physico-chemical point of view, cannot be completely separated from the latter by simple crystallisation.

The purification of the monocarboxylic and polycarboxylic aromatic acids is thus normally carried out by subjecting the crude product in aqueous solution (generally 20%) to a hydrogenation reaction with gaseous hydrogen in the presence of suitable catalysts, in order to convert the impurities into derivatives that are more easily separable from the desired end product, normally by crystallisation; this reaction is normally carried out at rather high temperatures (270° C. as regards the purification of terephthalic acid, approximately 220° C. for the purification of isophthalic acid).

Hydrogenation catalysts, which have to be capable of selectively hydrogenating the impurities while leaving the aromatic acid unaltered, are well known in the art; generally, they are metals belonging to group VIII (Perry, *Chemical Engineers' Handbook*, VI edition), preferably platinum, rhodium or palladium, normally supported on inert materials, such as on carbon or alumina; catalysts of this type are described in U.S. Pat. Nos. 3,522,298; 3,542,863; 3,584,039; 3,591,629; 3,607,921; 3,726,915; 3,799,976; 4,260,817.

U.S. Pat. No. 4,126,638 describes in particular a process for the purification of dicarboxylic aromatic acids by heterogeneous catalysts based on platinum, palladium, ruthenium, rhodium, iridium and/or osmium, operating in aqueous solution containing from 1 to 7% by weight of alcohol at a temperature of from 110 to 350° C.

U.S. Pat. No. 4,629,715 describes a process for the purification of crude terephthalic acid in aqueous solution by means of a heterogeneous catalyst based on palladium and rhodium, operating at temperatures of from 100 to 350° C. and at pressures of from 63 to 84 barge.

DESCRIPTION OF THE INVENTION

When only organic activators are used in the oxidation reaction, the crude aromatic acids so produced do not contain residual products which could damage the hydrogenation catalyst. However, the use of hafnium salts and in particular zirconium salts is at the root of a highly undesirable phenomenon which substantially limits the efficiency of the entire production process.

As described in the already mentioned U.S. Pat. No. 5,112,592 and WO 98/29378, the crude aromatic acids in fact contain a small portion of the above-mentioned zirconium and hafnium salts, generally acetates, as further impurities; those salts are unfortunately readily hydrolysable in aqueous solution, above all if subjected to elevated temperatures, of the order of from 200 to 300° C. Therefore, when the aqueous solution of the crude acid is introduced into the purification reactor, the hafnium and/or zirconium salts hydrolyse and precipitate on the hydrogenation catalyst in the form of insoluble colloidal polyoxides with the consequent poisoning of the catalyst (the service life of which is normally reduced by from 60 to 80%).

That disadvantage is normally limited by maintaining the concentration of the salts in the oxidation mixture at a value lower than 250 ppm, with obvious disadvantages from the point of view of production.

The object of the present invention is therefore to provide a process for the production of monocarboxylic and/or polycarboxylic aromatic acids which does not have the disadvantage indicated above, that is a process which, operating in the presence of a catalytic system containing hafnium and/or zirconium salts in concentrations which may be higher than 250 ppm, does not cause the poisoning of the hydrogenation catalyst used during the subsequent purification stage.

That result has now been achieved owing to the surprising observation that colloidal hafnium and/or zirconium polyoxides have a particularly high affinity to adsorbent substances, such as, for example, activated carbon, "Altapulcus Clay", titanium dioxide, alumina and/or silicon carbide; in particular, it has been observed that, by causing a suspension of colloidial hafnium and/or zirconium polyoxides to pass at a temperature of from 200 to 300° C. and at a pressure of from 30 to 90 barg through a column containing one or more of the above-mentioned substances, it is possible to achieve the complete adsorption of those polyoxides and, consequently, the complete purification of the solution concerned. The subject-matter of the present invention is therefore represented by a process for the production of monocarboxylic and polycarboxylic acids comprising a stage (a) for the oxidation of the corresponding aromatic precursors in liquid phase in the presence of gaseous oxygen and a catalytic system containing hafnium and/or zirconium salts and a subsequent stage (c) for the purification of the crude product so obtained by catalytic hydrogenation, comprising an intermediate purification step (b) in which the crude product resulting from stage (a) is supplied to a filling column (here defined as a "demetalliser") containing a bed of material having a high adsorbent power with respect to hafnium and/or zirconium polyoxides, operating at a temperature of from 200 to 300° C. and at a pressure of from 30 to 90 barg.

It should be pointed out in this connection that the intermediate purification step (b) may be carried out in conjunction with the various conventional oxidation and reduction processes, such as, inter alia, the various processes described in the patent documents indicated above, which are therefore to be regarded as included in the present description.

In the preferred embodiment of the present invention, once the filtration of the crude acid to be purified has been carried out, the acid is used for the preparation of a 15 to 25% by weight, preferably 20% by weight, aqueous suspension which is then supplied to the demetalliser at a pressure and temperature sufficient to achieve complete dissolution of the aromatic acid. The temperature will thus generally be from 200 to 300° C. while the pressure will be approximately from 30 to 90 barg, depending on the crude acid to be purified. In the case of terephthalic acid, a temperature of approximately 265 to 275° C., preferably 270° C., and a pressure of approximately from 65 to 75 barg, preferably 70 barg, tend to be reached; in the case of isophthalic acid, however, the operation is carried out at approximately from 215 to 225° C., preferably 220° C., and at approximately from 35 to 45 barg, preferably 40 barg.

The solution leaving the demetalliser, thus freed from any traces of hafnium and/or zirconium, is then supplied to the hydrogenation reactor where, in the presence of the appropriate catalyst, the purification of the polycarboxylic aromatic acids takes place; according to a preferred aspect of the present invention, the gaseous hydrogen introduced into the purification reactor generates a partial pressure approximately 5 to 6 times higher than the pressure of the solution containing the aromatic acid to be purified.

The solution leaving the purification reactor is then supplied to the crystallisation stage in order to permit the separation of the pure carboxylic acid.

Of the possible materials having an adsorbent action with respect to hafnium and zirconium polyoxides, activated carbon has been found to be the most efficient, because it completely removes the traces of hafnium and zirconium present in the crude polycarboxylic aromatic acids. Activated carbon has, inter alia, the advantage that it is easy to recover the metals absorbed by simple combustion; the oxides obtained can then be leached with acetic acid while the acetates of the metals can be recycled to the oxidation reactor. Excellent performances have also been obtained with alumina and, in particular, with Procatalyse A.A.2–5 Grade P alumina.

The process according to the present invention may be carried out either continuously or discontinuously, although the continuous method is preferred. In particular, this process is preferably used in conjunction with the process for the production of aromatic acids which is described in WO 00/58257.

Those and other aspects of the invention will be clear to any person skilled in the art; scheme 1 appended hereto and the Examples which follow are to be regarded purely as non-limiting illustrations of the invention.

EXAMPLE 1

1) Preparation of the demetalliser

A filling column (demetalliser) which had a volume of 10 liters and which was provided with a support grid for the absorbent material with holes having a diameter slightly smaller than the dimensions of the granules of the absorbent material, was cleaned thoroughly with dimineralised water. Before the introduction of the absorbent material, the demetalliser was filled with demineralised water up to the level predetermined for the total amount of absorbent material. The absorbent material, in this case 7 kg of activated carbon, was then introduced through a movable funnel which reached the level of the demineralised water (the mobility of the funnel is utilised to distribute the absorbent material in the demetalliser as uniformly as possible).

The bed of absorbent material was then washed with demineralised water until the water being discharged was absolutely free from solid particles.

2) The oxidation reaction

A reaction mixture containing 15% by weight of para-xylene, 80% by weight of glacial acetic acid and 5% by weight of H$_2$O was introduced continuously into an oxidation reaction having a volume of 10 liters; a quantity of cobalt acetate tetrahydrate equal to 3.8% by weight of the mixture and a quantity of zirconium acetate equal to 0.38% by weight of the mixture were then added to the mixture.

The oxidation reaction was carried out with air at a pressure of 6 barg and at a temperature of from 110 to 115° C.; the oxygen content of the air discharged at the outlet of the oxidation reactor was 5% by volume.

The suspension containing crude terephthalic acid was filtered continuously at a temperature of from 100 to 110° C. and at a pressure of 6 barg and was then washed at a pressure of 5 barg; the mother liquors were then recycled continuously to the oxidation reactor.

3) The purification stage

Only approximately from 11 to 15% of the zirconium originally present in the oxidation mixture were found to be present in the mother liquors resulting from filtration; the remaining 85–89%, however, remained as an impurity in the crude terephthalic acid.

The crude terephthalic acid was then dissolved in water to a concentration of 20%; the aqueous solution so obtained was then passed through the absorbent bed at a temperature of 270° C. and at a pressure of 70 barg; the solution leaving the demetalliser did not exhibit any detectable traces of zirconium.

The purified solution was then supplied to a purification reactor operating with gaseous hydrogen at a pressure of 75 barg and at a temperature of 270° C., in the presence of a heterogeneous catalyst based on palladium (0.5%) on a carbon support. The solution was then supplied to the crystalliser which separated crystalline terephthalic acid which had a content of 4-carboxybenzaldehyde of less than 25 ppm and which was practically free from palladium.

The same operations as those above were repeated without the intermediate passage through the demetalliser.

The terephthalic acid so obtained, although having a content of 4-carboxybenzaldehyde comparable to that of the previous example, was nevertheless characterised by a content of palladium of the order of a few ppm (confirming that the catalyser had been poisoned).

The life of the catalyst used in the process with an demetalliser was also 35% longer than that of the catalyst used in the comparison process.

What is claimed is:

1. A process for the production of monocarboxylic and/or polycarboxylic acids comprising the oxidation in liquid phase of the corresponding aromatic precursors in the presence of a catalytic system containing hafnium and/or zirconium salts and the subsequent purification of the crude product so obtained by catalytic hydrogenation, characterised in that it comprises an intermediate purification step in which the crude product resulting from the oxidation stage is supplied to a filling column containing a bed of material having a high adsorbent power with respect to hafnium and/or zirconium polyoxides, operating at a temperature of from 200 to 300° C. and at a pressure of from 30 to 90 barg.

2. A process according to claim 1, characterised in that the salts are acetates.

3. A process according to claim 1, characterised in that said catalytic system consists of a mixture of cobalt and zirconium salts, preferably acetates.

4. A process according to claim 1, characterised in that the material having a high adsorbent power with respect to hafnium and/or zirconium polyoxides is selected from activated carbon, "Altapulcus Clay", titanium dioxide, alumina and silicon carbide.

5. A process according to claim 1, characterised in that the crude product resulting from the oxidation stage is supplied to the filling column in the form of a 15 to 25% by weight aqueous solution.

6. A process according to claim 1, characterised in that the hafnium and/or zirconium salts are present in the aqueous solution in a concentration higher than 250 ppm.

7. A process according to claim 1, wherein para-xylene is oxidised to terephthalic acid.

8. A process according to claim 7, characterised in that the filling column operates at a temperature of from 265 to 275° C. and at a pressure of from 65 to 75 barg.

9. A process according to claim 1, wherein meta-xylene is oxidised to isophthalic acid.

10. A process according to claim 9, characterised in that the filling column operates at a temperature of from 215 to 225° C. and at a pressure of from 35 to 45 barg.

11. A process according to claim 1, characterised in that the gaseous hydrogen introduced into the purification reactor generates a partial pressure 5 to 6 times higher than the pressure of the solution containing the crude acid to be purified.

12. A process according to claim 5, characterised in that, prior to the preparation of the aqueous solution, the crude acid resulting from the oxidation stage is filtered at a pressure of from 1 to 20 barg and at a temperature of from 90 to 150° C.

* * * * *